(12) United States Patent
Jagadevan

(10) Patent No.: US 10,881,122 B2
(45) Date of Patent: Jan. 5, 2021

(54) GRINDING DEVICE WITH SELF-CLEANING AND FERMENTATION ASSIST AND METHODS OF USING THE SAME

(71) Applicant: Karthikeyan Jagadevan, Greenwood, IN (US)

(72) Inventor: Karthikeyan Jagadevan, Greenwood, IN (US)

(*) Notice: Subject to any disclaimer, the term of this patent is extended or adjusted under 35 U.S.C. 154(b) by 278 days.

(21) Appl. No.: 15/989,170

(22) Filed: May 24, 2018

(65) Prior Publication Data

US 2018/0338516 A1      Nov. 29, 2018

Related U.S. Application Data

(60) Provisional application No. 62/510,510, filed on May 24, 2017.

(51) Int. Cl.

| | | |
|---|---|---|
| *A23L 7/10* | (2016.01) | |
| *B02B 1/04* | (2006.01) | |
| *B02C 23/18* | (2006.01) | |
| *A23L 7/104* | (2016.01) | |
| *B02C 4/16* | (2006.01) | |
| *B02C 4/06* | (2006.01) | |
| *B02C 23/40* | (2006.01) | |
| *B02C 9/00* | (2006.01) | |
| *A61K 38/20* | (2006.01) | |
| *C07K 16/46* | (2006.01) | |
| *B02C 15/14* | (2006.01) | |

(52) U.S. Cl.
CPC ............ *A23L 7/197* (2016.08); *A23L 7/104* (2016.08); *A61K 38/2013* (2013.01); *B02B 1/04* (2013.01); *B02C 4/06* (2013.01); *B02C 4/16* (2013.01); *B02C 9/00* (2013.01); *B02C 23/18* (2013.01); *B02C 23/40* (2013.01); *C07K 16/46* (2013.01); *A23V 2002/00* (2013.01); *B02C 15/14* (2013.01)

(58) Field of Classification Search
CPC ................................ A23L 7/197; B02C 23/18
See application file for complete search history.

(56) References Cited

U.S. PATENT DOCUMENTS

| | | | | |
|---|---|---|---|---|
| 3,519,052 A | * | 7/1970 | Girgis | .................... B02B 3/08 99/610 |
| 5,522,913 A | | 6/1996 | Peguy | |

(Continued)

FOREIGN PATENT DOCUMENTS

WO     WO-2016199498 A1 *  12/2016  .............. B22C 5/08

OTHER PUBLICATIONS

English translation WO 2016199498A1 (Year: 2016).*

*Primary Examiner* — Jason L Vaughan
*Assistant Examiner* — Amanda Kreiling
(74) *Attorney, Agent, or Firm* — Ryan Alley IP

(57) ABSTRACT

Automated grinder systems include several different automatic functions including liquid and substrate soaking, mixing, grinding, fermenting, and cleaning. Example grinders include storages for soaking and draining a substrate for grinding, a water or other fluid reservoir connected to provide soaking material, and a grinder connected to the storage to receive and grind the substrate. A resting unit may receive the ground batter and potentially ferment the same by controlling its temperature, humidity, pH, etc. Jets may be connected to a water reservoir and direct liquid water into the grinder, potentially with soap, to cleanse the same.

25 Claims, 17 Drawing Sheets

(56) References Cited

U.S. PATENT DOCUMENTS

Figure 1:
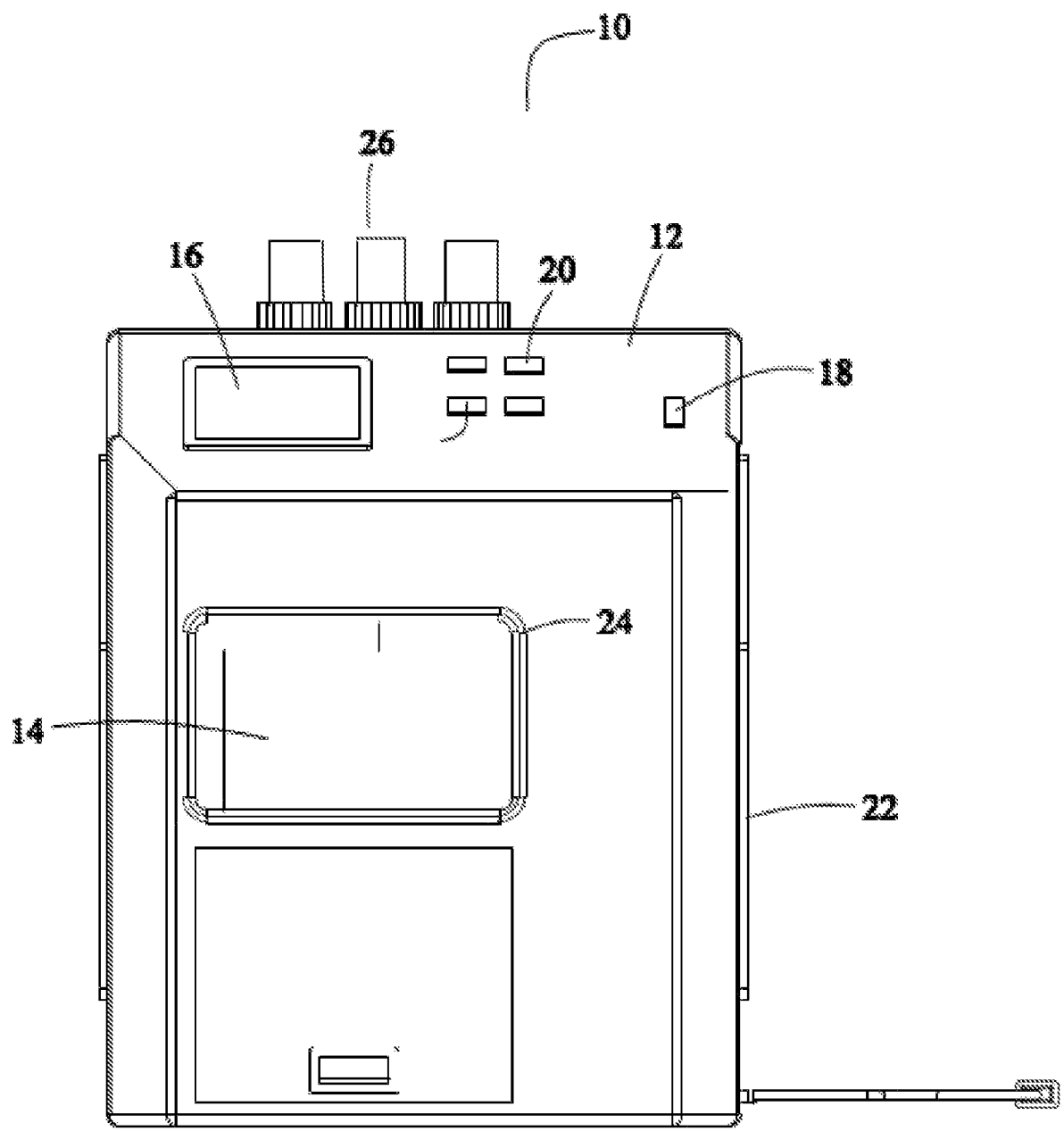

| | | |
|---|---|---|
| 7,851,210 B2 | 12/2010 | Darling et al. |
| 9,334,545 B2 | 5/2016 | McDonald et al. |
| 2012/0095595 A1 | 12/2012 | Krishnan |
| 2013/0260433 A1 | 10/2013 | Zhang |

* cited by examiner

GRINDING DEVICE WITH SELF-CLEANING AND FERMENTATION ASSIST AND METHODS OF USING THE SAME

RELATED APPLICATIONS

This application claims priority under 35 U.S.C. § 119 to U.S. Provisional Application 62/510,510, filed May 24, 2017 and incorporated by reference herein in their entireties.

BACKGROUND

Preparing batter-based food conventionally includes soaking ingredients, like rice, lentils, etc., grinding them to a desired consistency to produce a batter, and optionally fermenting the batter. In some methods of making batter, an estimated or a measured quantity of dry ingredients are soaked in water, and then the soaked ingredients are ground for producing batter. The quality of the batter produced is typically measured by its consistency and its final physical appearance. Several variables affect the quality of the batter including the ratios of the ingredients used, time used for soaking the ingredients, quantity of water used, and how much water is added at intervals while preparing the batter.

Grinding stones and rollers have been used for creating batter through a laborious and skill intensive process. It takes years of practice for a person to achieve required proficiency of a batter using such wet grinding machines. Now, household appliances are being widely adapted for automated food preparation, including grinding and batter production. For example, electrically-operated mixers and grinders may perform a standardized function of grinding and mixing, with the remainder of the batter-production executed manually, including deciding the ratio and combination of the ingredients such as lentils, rice etc., pre-soaking, loading the ingredients in the grinder drum, removing and cleaning the grinder, resting the batter for fermentation, if required, and cleaning the grinder.

Conventional automatic grinding devices might include a grinder drum with a set of grinding rollers powered by an electric motor inside the grinding drum, which rotates along a fixed horizontal axis for grinding the ingredients. The grinder drum itself is provided with an electric motor to rotate on an axis perpendicular to the rotating axis of grinding rollers. Once ground into a batter, even fermentation may be ensured by a controlled environment and constant monitoring of the batter.

SUMMARY

Example embodiments and methods include automated grinder systems with several different automatic functions including liquid and substrate soaking, mixing, grinding, fermenting, and cleaning. Example grinders include storages for soaking and draining a substrate for grinding, a water or other fluid reservoir connected to provide soaking material, and a grinder connected to the storage to receive and grind the substrate. A resting unit may receive the ground batter and potentially ferment the same by controlling its temperature, humidity, pH, etc. Jets may be connected to a water reservoir and direct liquid water into the grinder, potentially with soap, to cleanse the same.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

Figure 2:
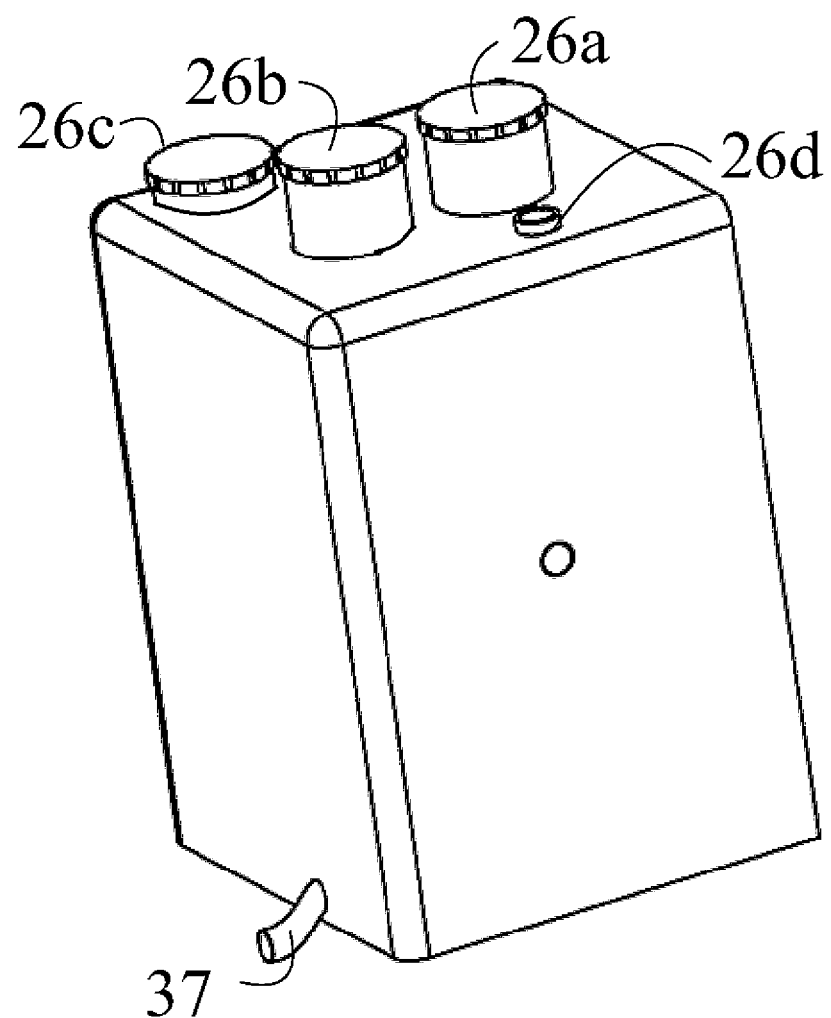
Figure 3:
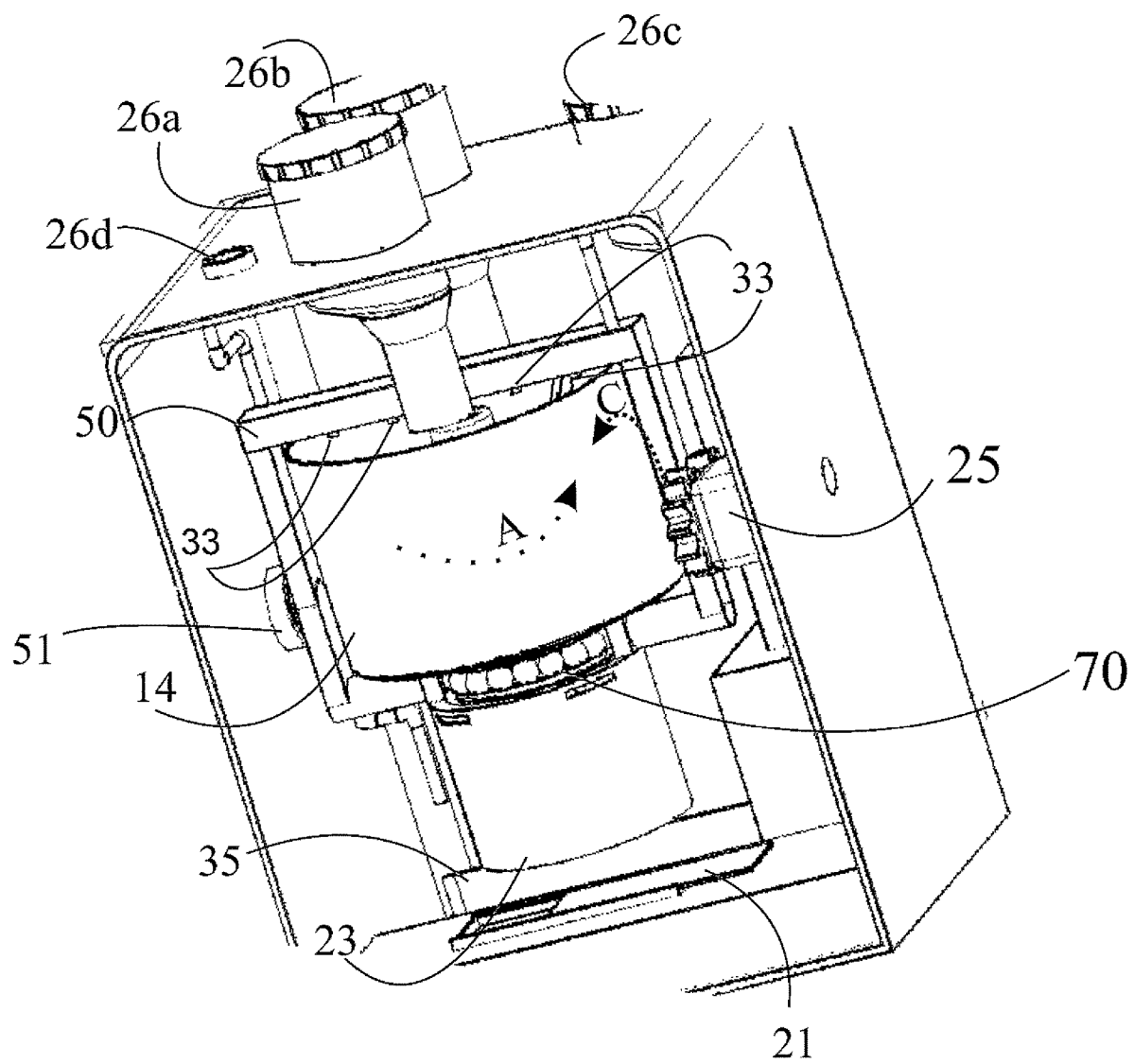
Figure 4:
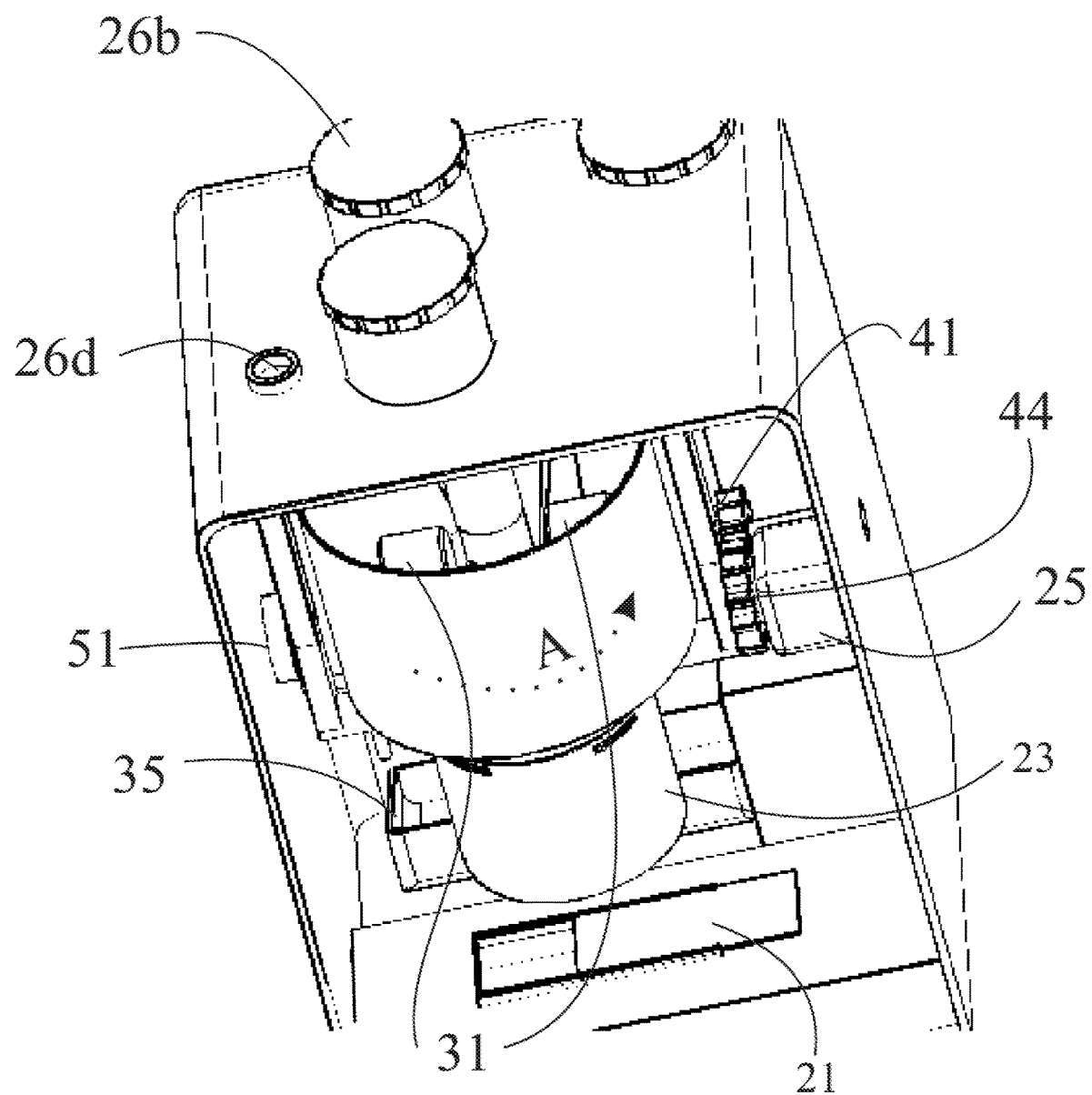
Figure 5:
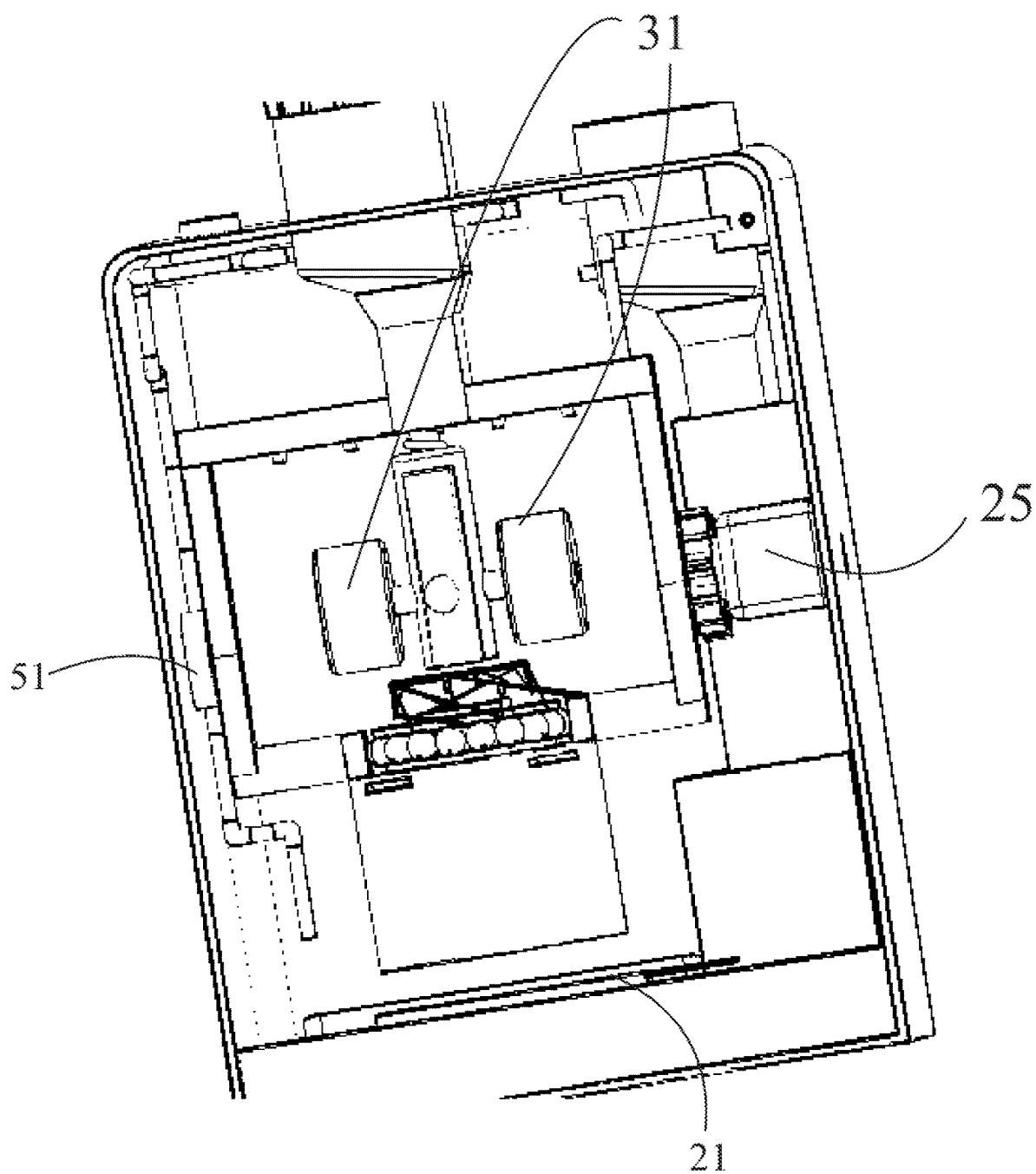
Figure 6:
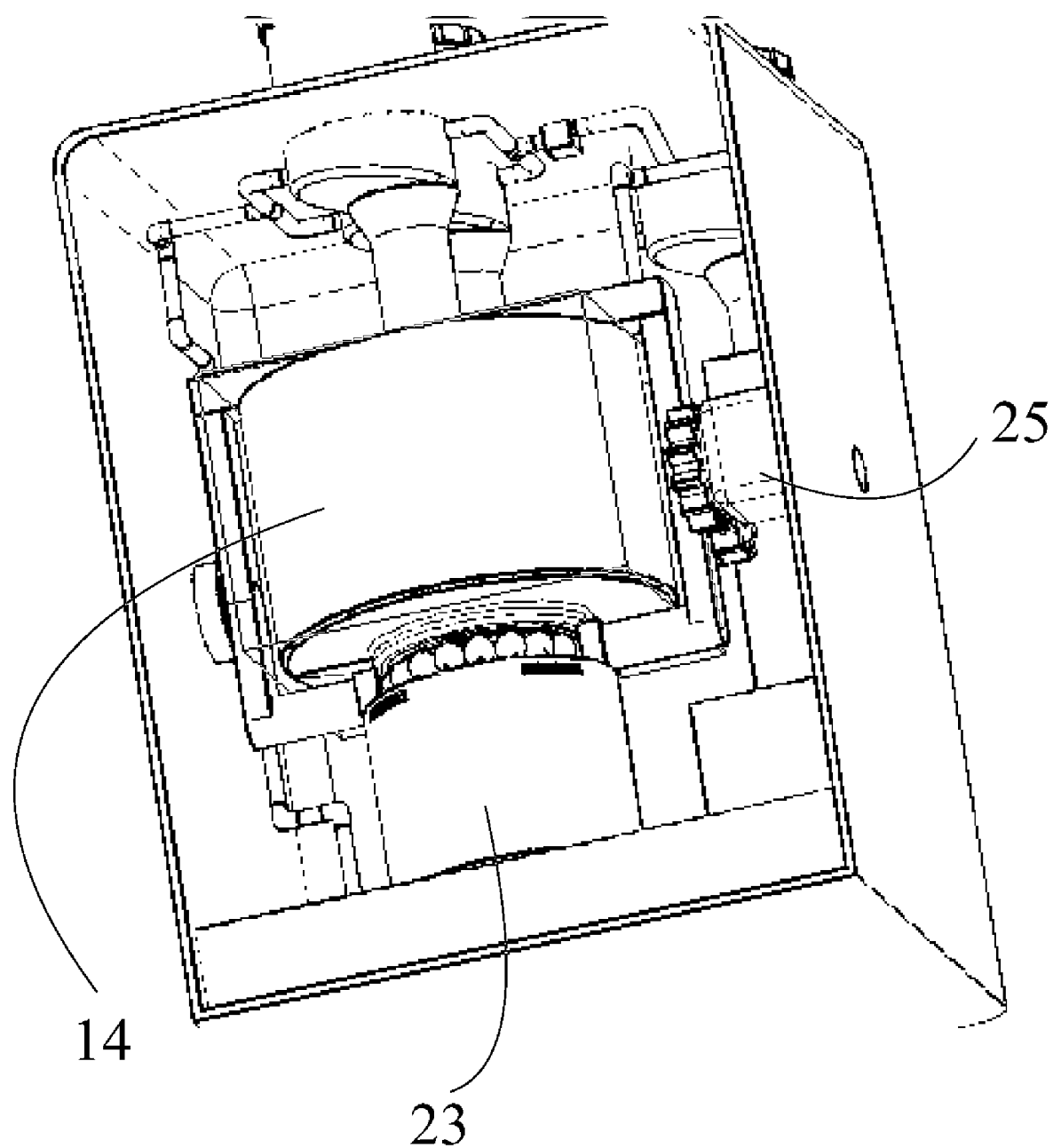
Figure 7:
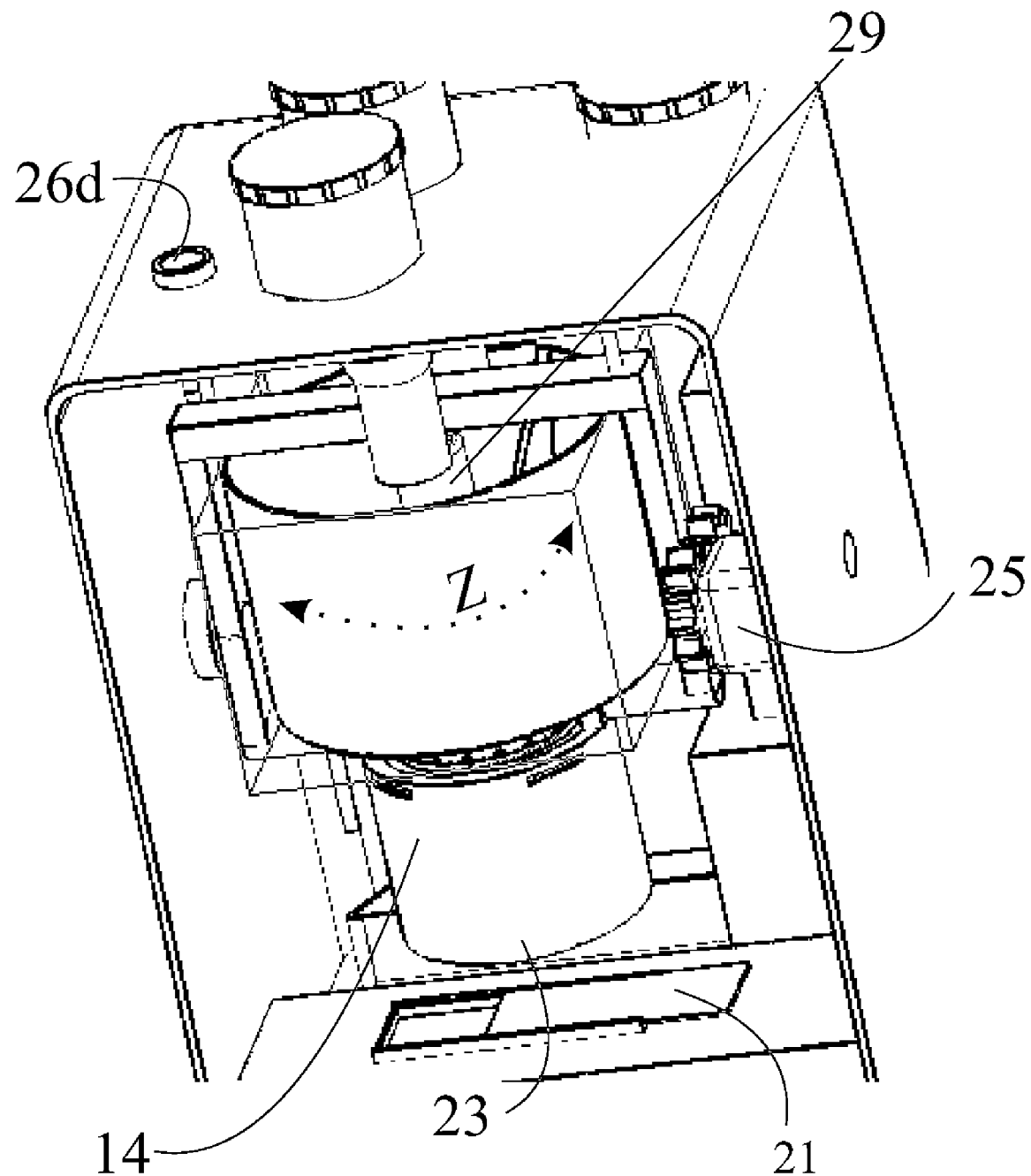
Figure 8:
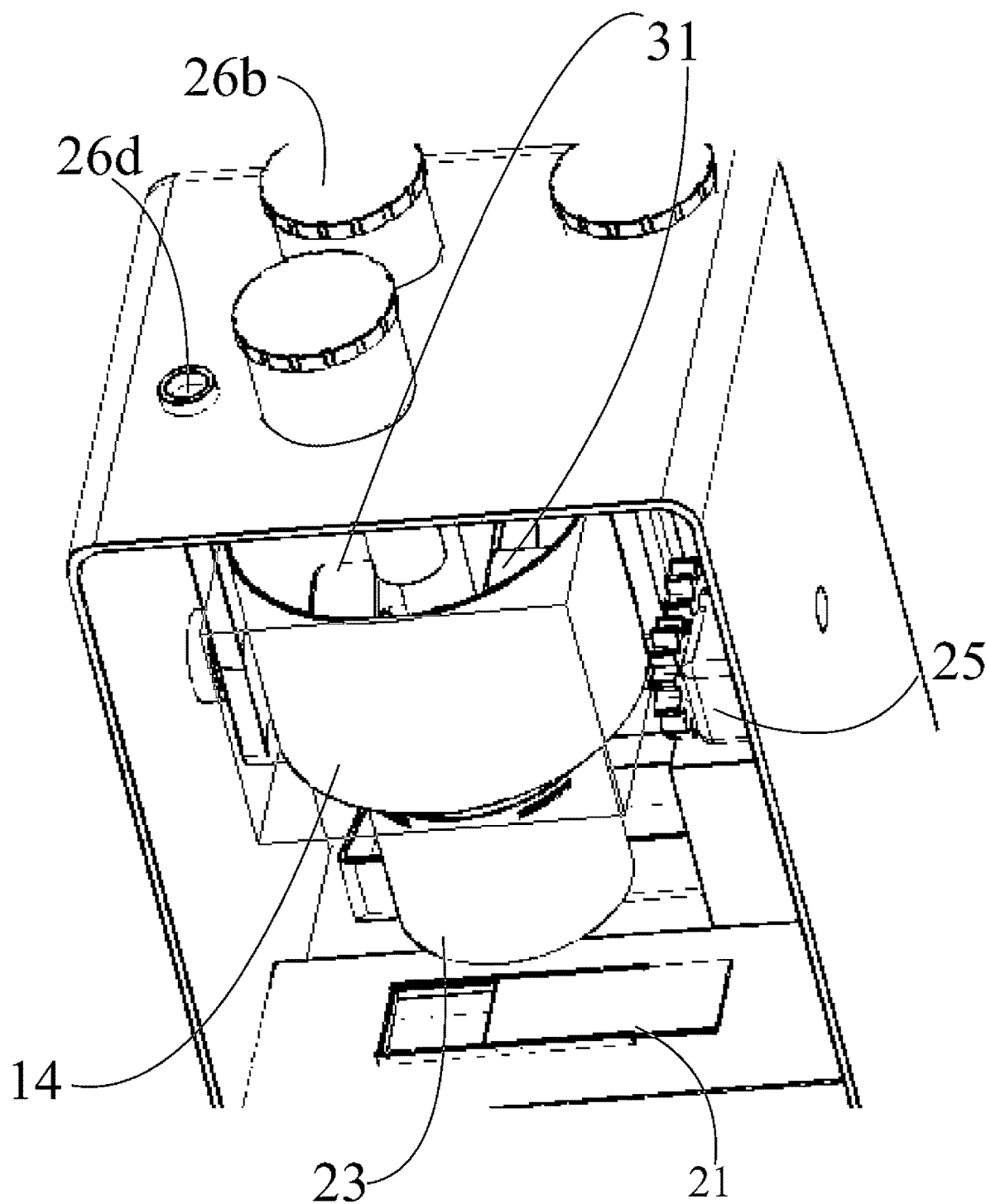
Figure 9:
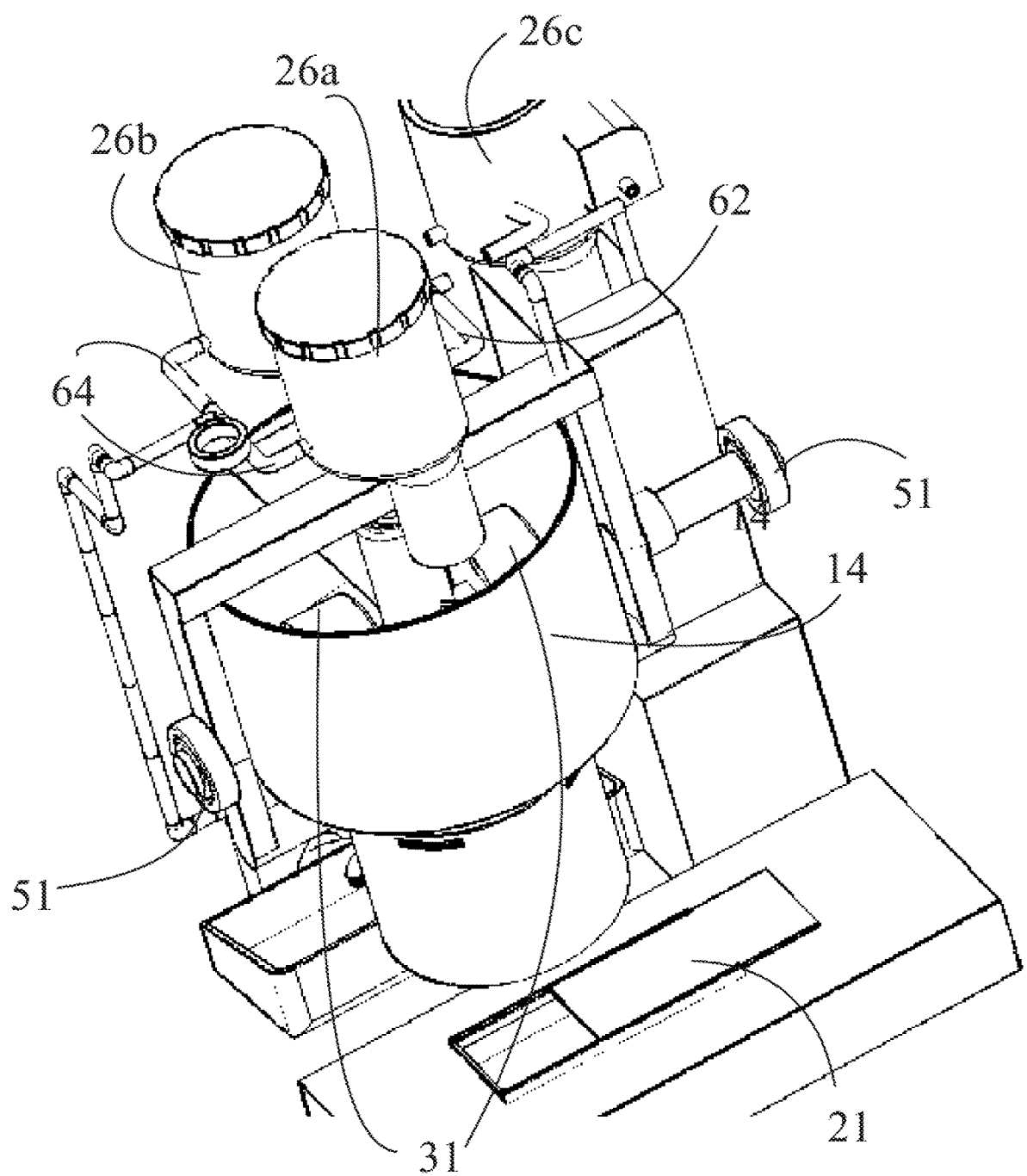
Figure 10:
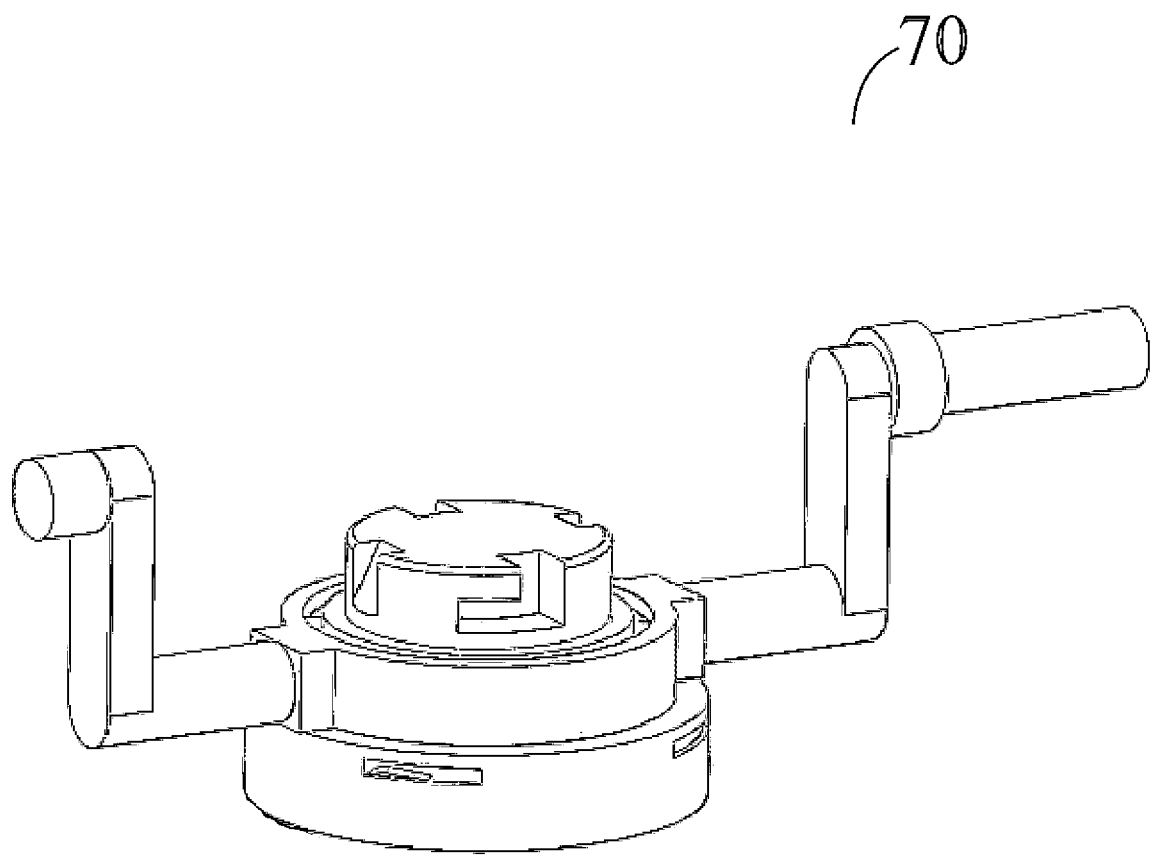
Figure 11:
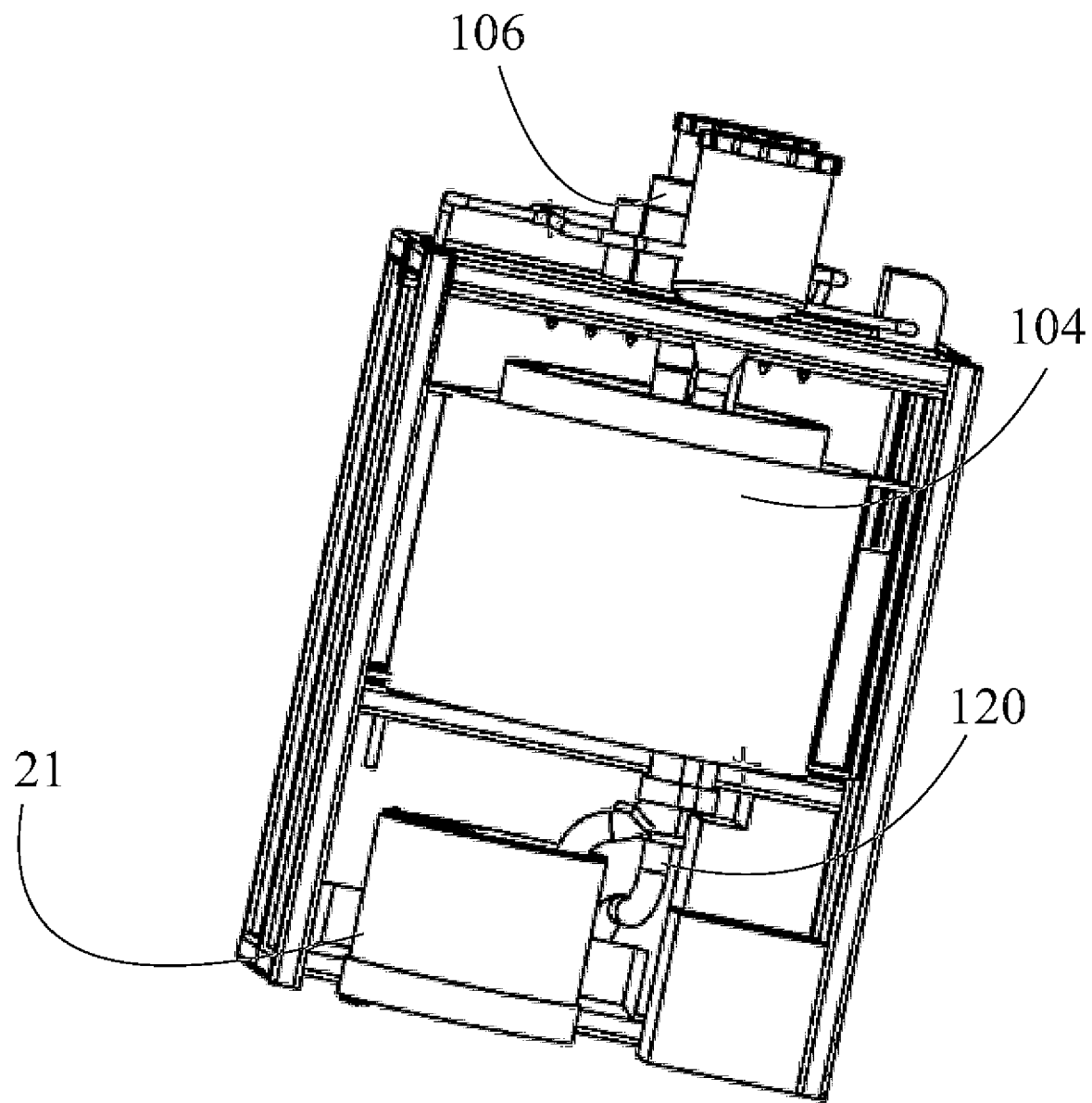
Figure 12:
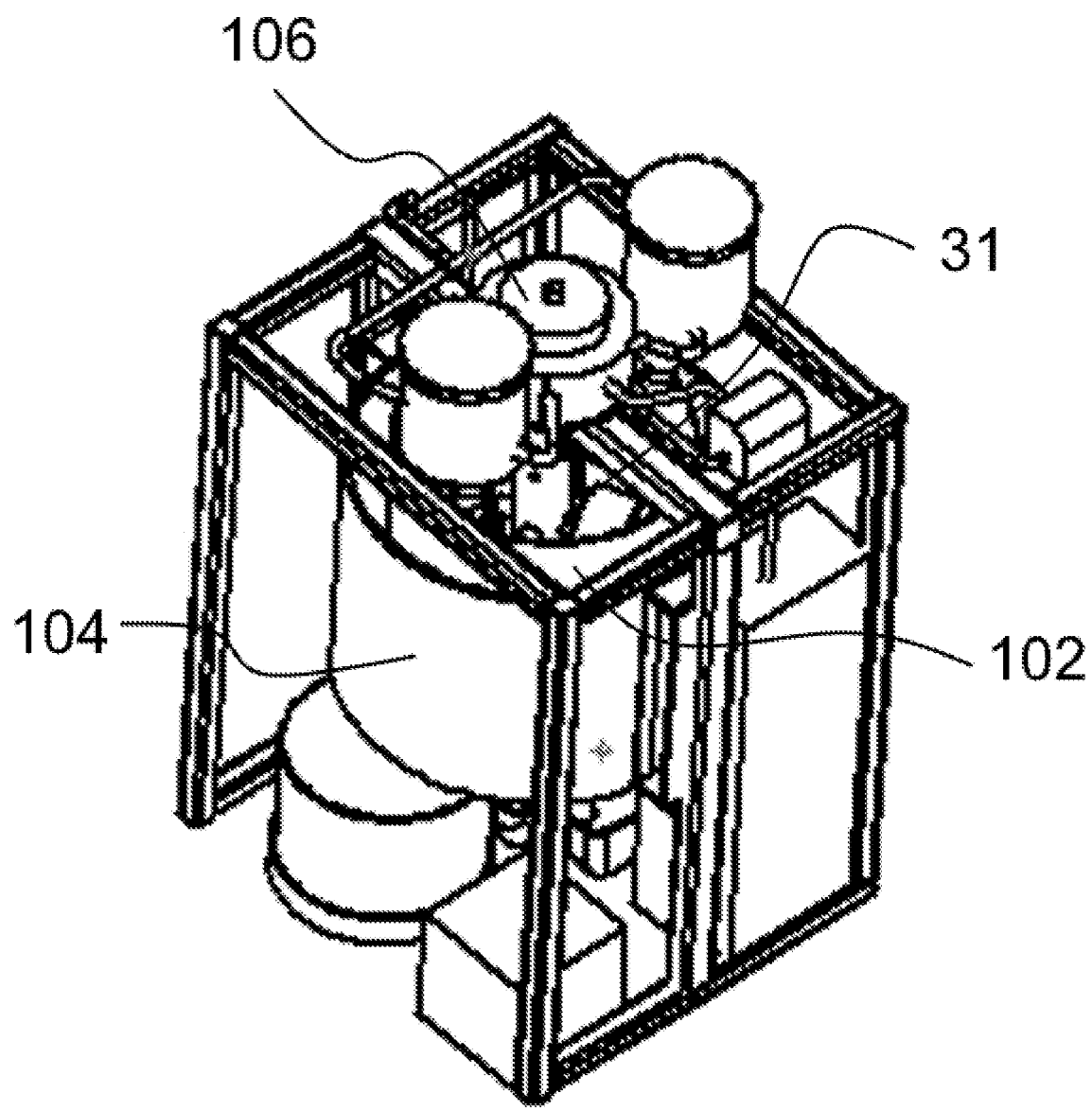
Figure 13:
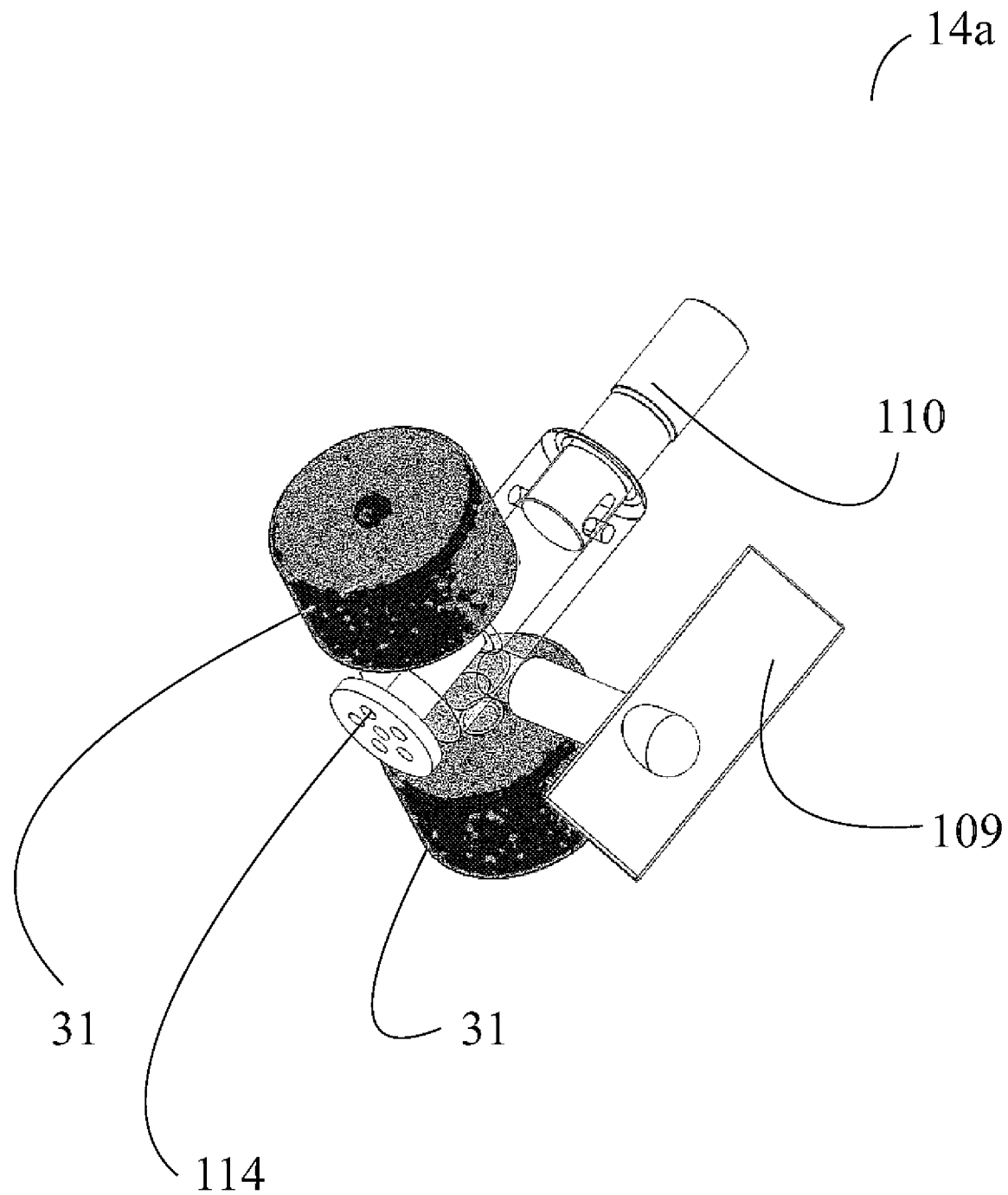
Figure 14:
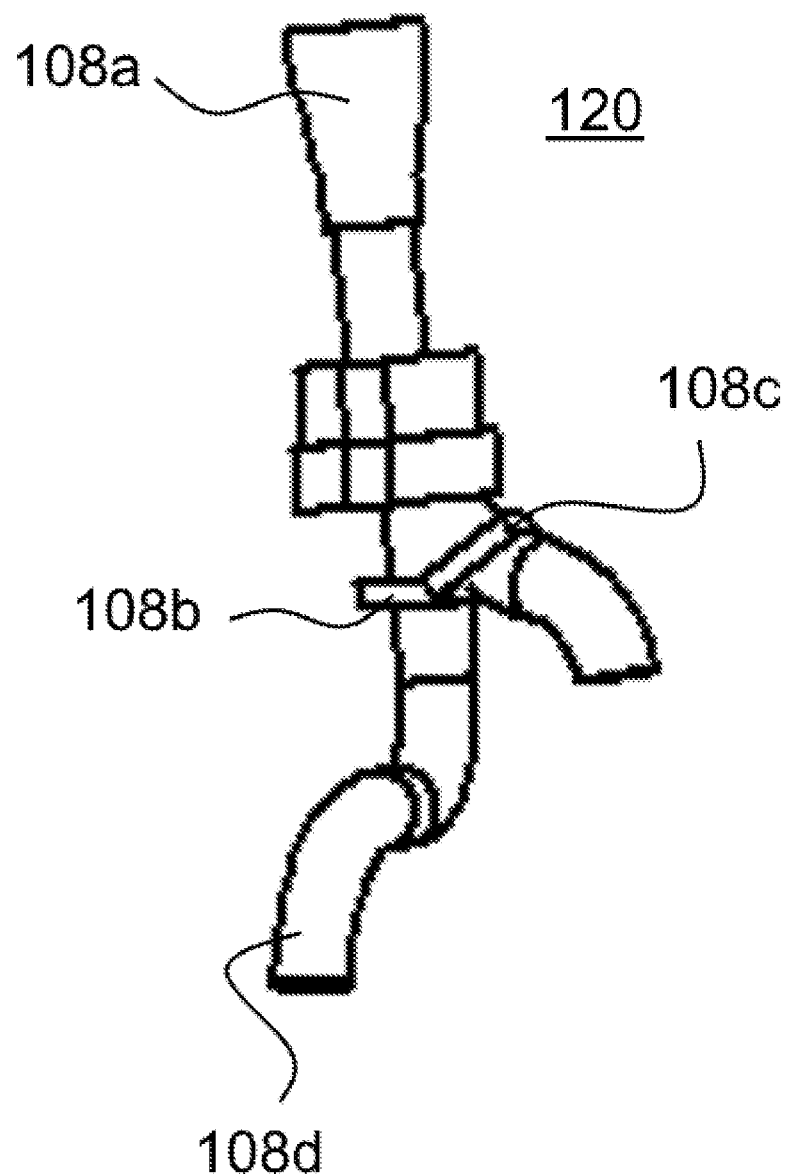
Figure 15:
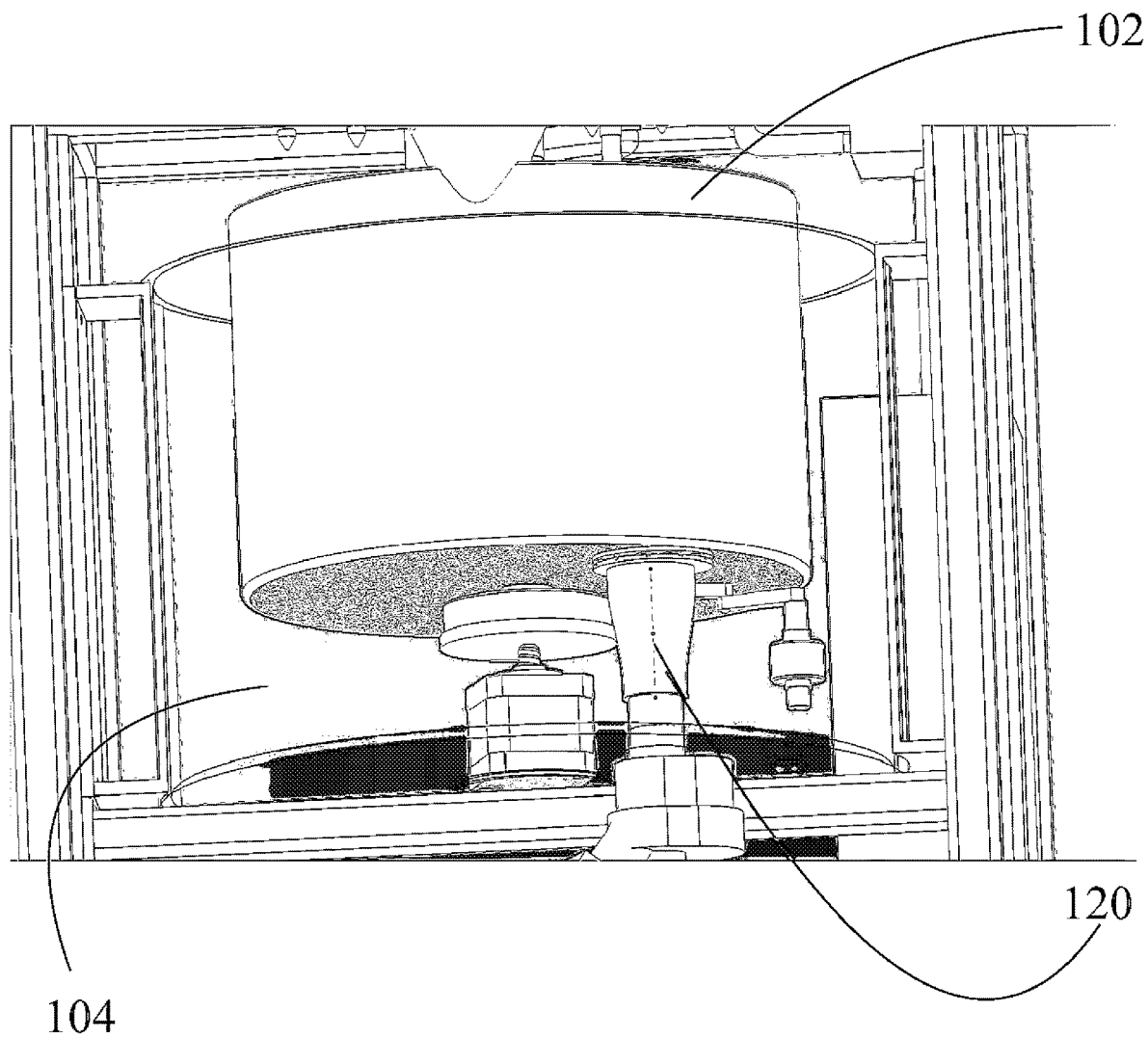
Figure 16:
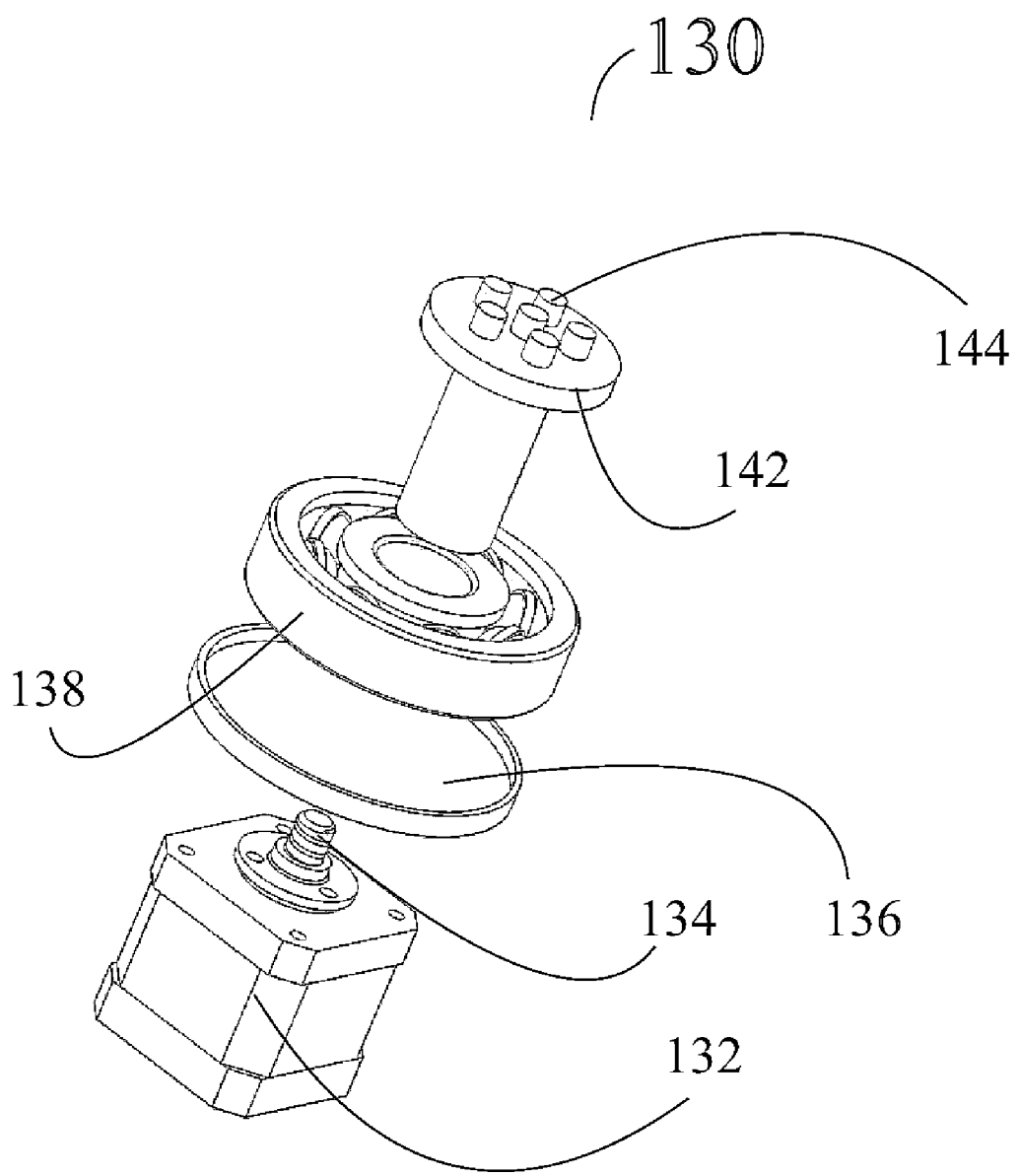
Figure 17:
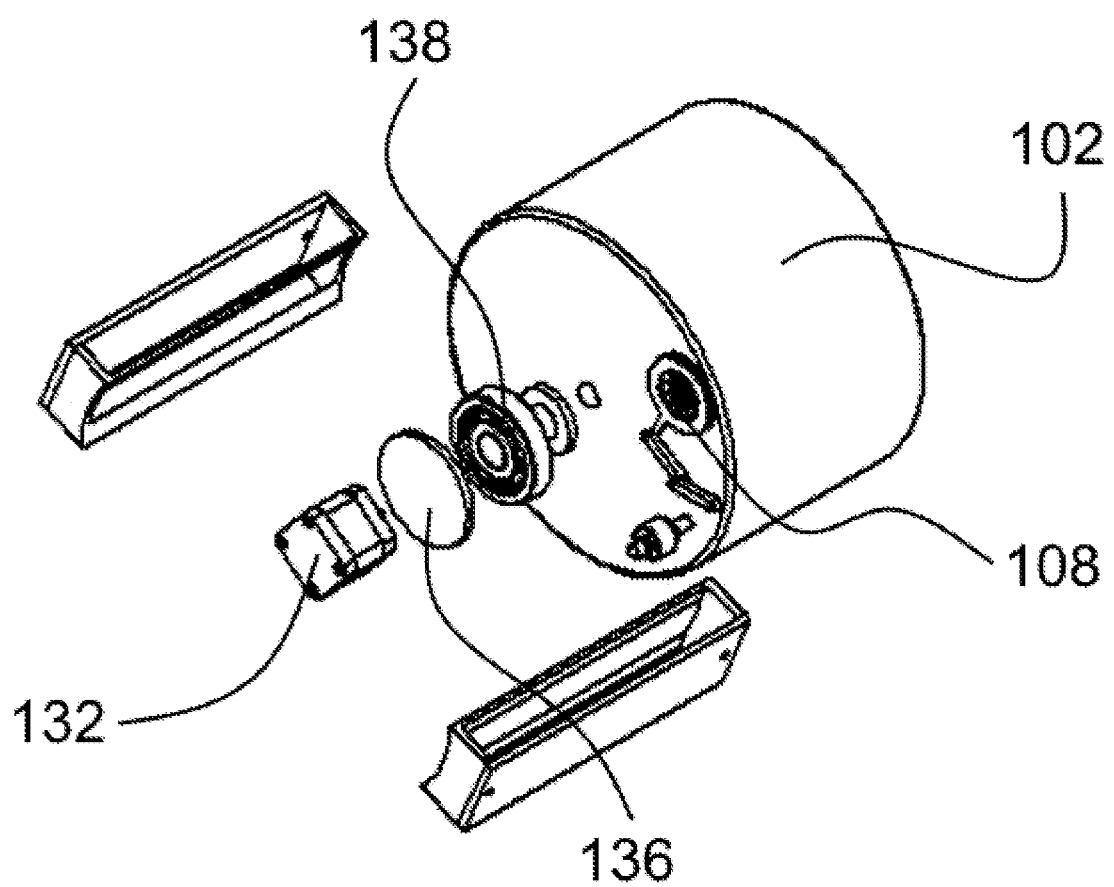

FIG. 1 is a front view illustration of an example embodiment grinder system.
FIG. 2 is a rear view illustration of the grinder of FIG. 1.
FIG. 3 is a front open view of the grinder of FIG. 1.
FIG. 4 is another view of the grinder of FIG. 3.
FIG. 5 is an internal view of the grinder of FIG. 3.
FIG. 6 is a bottom view of the grinder of FIG. 3
FIG. 7 is an internal view of the grinder of FIG. 1.
FIG. 8 is another internal view of the grinder of FIG. 7.
FIG. 9 is an illustration of a coupler between motor and grinder.
FIG. 10 is an internal view of the internal pipes of the grinder of FIG. 1.
FIG. 11 illustrates an alternative embodiment grinder system.
FIG. 12 illustrates a top view of the grinder of FIG. 11.
FIG. 13 is an illustration of a grinding roller unit of the grinder of FIG. 11.
FIG. 14 illustrates an example embodiment dispensing pump.
FIG. 15 is a detail illustration of the dispensing pump of FIG. 14.
FIG. 16 is an exploded view of a clutch and locking system for engaging and disengaging the grinding roller unit with respect to the inner drum.
FIG. 17 is an exploded view of the inner drum and the outer drum along with the bearing and clutch and locking system.

DETAILED DESCRIPTION

Because this is a patent document, general broad rules of construction should be applied when reading it. Everything described and shown in this document is an example of subject matter falling within the scope of the claims, appended below. Any specific structural and functional details disclosed herein are merely for purposes of describing how to make and use examples. Several different embodiments and methods not specifically disclosed herein may fall within the claim scope; as such, the claims may be embodied in many alternate forms and should not be construed as limited to only examples set forth herein.

It will be understood that, although the terms first, second, etc. may be used herein to describe various elements, these elements should not be limited to any order by these terms. These terms are used only to distinguish one element from another; where there are "second" or higher ordinals, there merely must be that many number of elements, without necessarily any difference or other relationship. For example, a first element could be termed a second element, and, similarly, a second element could be termed a first element, without departing from the scope of example embodiments or methods. As used herein, the term "and/or" includes all combinations of one or more of the associated listed items. The use of "etc." is defined as "et cetera" and indicates the inclusion of all other elements belonging to the same group of the preceding items, in any "and/or" combinations.

It will be understood that when an element is referred to as being "connected," "coupled," "mated," "attached," "fixed," etc. to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion e.g., "between" versus "directly between," "adjacent" versus "directly adjacent," etc. Similarly, a term such as "communicatively connected" includes all variations of information exchange and routing between two electronic devices, including intermediary devices, networks, etc., connected wirelessly or not.

As used herein, the singular forms "a," "an," and "the" are intended to include both the singular and plural forms, unless the language explicitly indicates otherwise. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

The structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, so as to provide looping or other series of operations aside from single operations described below. It should be presumed that any embodiment or method having features and functionality described below, in any workable combination, falls within the scope of example embodiments.

The inventors have recognized that existing wet grinders make it very difficult to get a good quality batter with proper consistency for a user, typically requiring years of experience to so. There are few clear guidelines, including quantity of ingredients that should be added, the grinding time, or amount of water to be added. Due to this a grinder often halts or slows down during the grinding process as overloaded. This mid-process shutdown is very inconvenient, and it is often unpleasant and interrupting to partially remove contents from the grinding drum to avoid it. This may lead to a longer grinding process and additional labor. Even fully-automatic wet grinders may suffer from this lack of clarity and requirement for load readjustment, which may require continuous human intervention and time.

Based on the foregoing, the Inventors have newly recognized a need for a fully automatic grinding device that does not require intervention or constant monitoring. There needs to be automation in selection and grinding of ingredients, water control, temperature control during grinding and resting of batter, and automatic cleaning at the end of the process. Remote monitoring, such as through Wi-Fi or Bluetooth, is also needed. The inventors have developed example embodiments and methods described below to address these and other problems recognized by the Inventors with unique solutions enabled by example embodiments.

The present invention is automatic grinder systems having several distinct automated functions and methods of using the same. In contrast to the present invention, the few example embodiments and example methods discussed below illustrate just a subset of the variety of different configurations that can be used as and/or in connection with the present invention.

Example embodiments provide automatic grinding and self-cleaning devices, potentially with fermentation assist, including a housing, storage for ingredients, grinder, grinding roller, resting unit, fixed ladle for mixing batter during grinding, drain, display, controller, thermostat, control buttons, soap dispenser, interconnected pipe lines, and/or power source. Ingredients may be added in the storage unit and dispensed into the grinder through user input. The time required for grinding may also be controlled by the user. Upon completion of the grinding process, the resultant batter may be emptied into a resting unit. This is followed by cleaning of the grinder and the grinding roller.

The resting unit may be associated with a thermostat and/or heater to maintain temperature and with a humidity sensor and/or humidifier to maintain humidity for assisting fermentation process inside the resting unit. Batter produced may be kept in the resting unit under controlled temperature monitored by the thermostat for aiding fermentation over a desired time. When the temperature is controlled during fermentation, the time required to obtain a good quality batter with appropriate consistency is reduced with precision. Fast fermentation, such as within 4-7 hours may be achieved through such control, opposed to the conventional 3-13 hours at uncontrolled room temperature, or even 16-20 hours when the room temperature is less than 27 degrees Celsius, such as during winter.

FIG. 1 is a perspective view of example embodiment grinder system 10. As shown in FIG. 1, grinder system 10 may include a housing 12, storages 26*a*, 26*b*, 26*c* (FIG. 2), grinder 14, a grinding roller, display 16, micro-controller or processor, thermostat, control buttons 20, soap dispenser 26*d*, interconnected pipe lines, and/or a control module. Ingredients may be stored in storage 26 and dispensed therefrom by a user's input. If storage 26 is empty, such as if the ingredients are not added, for the appropriate selection, an error message may appear on display 16. The user may input a selection of a type of batter and the amount of batter to make through inputs such as control buttons or display 16 that is touch-enabled.

As shown in FIG. 2, multiple storages 26*a*, 26*b*, 26*c* may be aligned on a single top surface. Storages 26 may be gravity-fed and used to store a substrate, such as a grain, for batter preparation and water for soaking the same before it is ground. For example, first storage 26*a* may contain grain that feeds by rationing, according to desired proportions by weight, and after the grain has been adequately soaked for the purposes of grinding. Second storage 26*b* may include water or another liquid and may be communicably coupled to first storage 26*a* for soaking the grain in 26*a*. Soaked grain may be releasably dispensed with a motor-driven flap at a bottom of the first storage 26*a*. The flap may default to a closed position so that water is retained in storage 26*a* and soaks the grain. After soaking, the water may be discharged, and the motor may then actuate the flap from the closed position to an open position to dispense the soaked grain.

Several storages 26 may be provided to add a combination of grains or other substrates to create the batter. Storages 26 may be communicably coupled. Each storage 26 may have a similar selective discharge flap as described above. Grinder 14 is configured to receive matter from any of the storages in any combination.

To adequately soak the ingredients from first storage 26*a* and additional storage 26*b*, each storage 26 may include valves to allow entry and exit of water. These valves may open and/or close in a time-controlled fashion, based on an amount of soaking required per ingredient. Further, water from storage 26 may be used for cleaning, soaking, and/or grinding.

Several valves 62 (FIG. 9) may reliably control fluid movement and release. Valves 62 may be controlled by a timer to effect their opening and closing. Pipes 64 (FIG. 9) may connect water storage 26c to first storage 26a, for example, or water storage 26c to second storage 26b to facilitate soaking. Pipes 64 may also connect first storage 26a to drain 35 to drain out waste water after a soaking/rinsing cycle; such drain connection may be used for each storage 26.

For example, first valve 62 may be located toward an exit of water from storages 26a and 26b to allow water to exit storages 26a and 26b after soaking time is over. Or, for example, second valve 62 may be located toward an extreme bottom portion of storage 26a or 26b to remove soaked and drained ingredients from storage 26a and 26b into grinder 14 below it. For example, a sieve valve and/or seal valve may be used. These valves may be closed by default.

Once the ingredients are added, a water line may open, through pipes 64 to rinse the ingredients and clean. A seal valve may remain open while a sieve valve is closed to release the dirty water to be drained through the second set of pipes to drain 35. Then, the seal valve may close. This valve and seal opening and closing may be achieved by a computer-based controller with preset soaking times for various types of batter and mixtures. After the soaking process, a water sprayer may cleanse the grinder. Finally, the seal and sieve valves may open and the soaked ingredients may drop in grinder 14. Water storage 26c may include a single valve to dispense water from it into other storages 26a or 26b or grinder 14.

A sieve (not shown) may be positioned at a bottom of each of first storage 26a and second storage 26b to allow water to enter the grinding drum after it has been soaked. This water is waste water and may be disposed before the ingredients are introduced into the grinder 14 for grinding into batter. The drum of grinder 14 may be tilted toward drain 35 in this instance, as discussed below.

Storages 26a and 26b may include an agitator (not shown) to agitate the storages to properly rinse and/or soak the ingredients once filled with water. The agitator may be timed with the closure of valve 62 and thus holding of water in storages 26a and/or 26b. The agitator may be a simple flow agitator, for example. Alternatively, pressurized water may be used without an agitator.

Example embodiment grinder system 10 may include a frame 50 or housing, with grinder 14 placed below storages 26 in the same. Grinder 14 is configured angularly displace, or rotate, about a first axis or in a first degree of freedom while grinding. For example, this movement may be clockwise or anticlockwise, as shown by reference numeral A in FIG. 3, and grinder 14 may be limited to this motion only while grinding. Motor 23 may drive this rotation of grinder 14, under the control of a processor or control module.

Grinder 14 may also be tilted about a different axis of rotation, potentially one orthogonal to the grinding axis, shown by reference letter C. Grinder 14 may also be attached to stepper motor 25 attached on the side of frame 50. Stepper motor 25 may grinder 14 about this different axis C.

Storage 26a may include a weight load sensor to measure the quantity of contents added to storage 26a. The load sensor allows measurement of quantities of ingredients, ensuring correct amounts are used. This may eliminate motor overloading. For example, first storage 26a may include a disposal portion extending toward grinder 14, and a load sensor may be located toward a bottom of storage 26a at this portion. Similarly, water storage 26c may include a water level sensor to allow a user or controller to know water level available or if a refill is needed. The controller may be programmed or otherwise configured with settings of quantity of ingredients and water from the storages. Additional items in other storages may be programmed to earmark ratios for customized grinding.

As shown in FIG. 7, grinder 14 may be configured to angularly displace or rotate in a second direction opposite to the first direction. This dual angular displacement motion, shown by reference Z in FIG. 7, such as agitation with rotation back and forth in opposite directions about a same axis, may aid cleaning grinder 14.

As shown in FIG. 3, grinder 14 may angularly displace about a different axis, or in a second degree of freedom. This second degree of freedom may permit the batter to be poured into resting unit 21 below grinder 14. Reference numeral C illustrates this direction. Resting unit 21 and drain 35 are both located below the grinder 14 such that when grinder 14 tilts or rolls in a first direction of the second degree of freedom, it pours its contents or portion thereof into drain 35 and when grinder 14 tilts or rolls the other direction in the second degree of freedom, it pours its contents or portion thereof into resting unit 21. Still further, grinder 14 may move in any or all six degrees of freedom. Operative bottom side of grinder 14 is fitted with a pan cake motor which can sustain high loads and provide high torques.

Resting unit 21 may include a pH sensor to sense pH level of the batter, a viscosity sensor to sense viscosity of the batter, a humidity sensor to sense humidity of the batter, and/or a temperature sensor to sense temperature of the batter. All of these sensors may be used to adjust resting time and change temperature, humidity, etc. of resting unit 21 for desired fermentation and other batter characteristics, potentially automatically by a processor. For example, resting unit 21 may include a heating element, such as an IR light, to heat resting unit 21 to aid fermentation of batter therein. A humidifier and/or a dehumidifier may be provided in resting unit 21. Or, for example, a cooling element may be located in resting unit 21 to cool the batter as desired. Thus, an optimum temperature and other fermentation characteristics can be achieved and the problems of over fermenting in warm climates and under fermenting in cold climates avoided. These systems may be monitored and controlled using a thermostat and other sensors connected to the controller, where all sequence and settings are computed, stored, and/or executed.

In example embodiment grinder system 10, the grinding roller 31 may be located inside grinder 14 to enable grinding of the substrate. As shown in FIGS. 7 and 13, the grinding roller may be grinding stones at the end of shaft 29. Shaft 29, and hence the grinding stones, may be configured to be angularly displaced, or rotate, opposite to grinder 14 about a same axis. For example, if grinder 14 angularly displaces by a motor clockwise, the internal grinding roller may rotate counterclockwise. to provides the grinding action. Grinding roller shaft 29 and stones thereon may of course move in any other fashion, about any or all six degrees of freedom.

Grinder 14 may receive support from frame assembly 50 surrounding grinder 14 periphery. Frame assembly 50 derives support from the internal walls of housing 22. Bearings 51 allow for tilting grinder 14. Bearings 51 are laterally located with respect to grinder 14 and derive support from frame assembly 50.

Grinding roller 31 are held by shaft 29 connected from the bottom with the motor 21. Coupling mechanism 70 may couple motor 21 to grinder 14. Motor 21 may also tilt along with grinder 14. Coupler 70 may be supported by frame assembly 50. First set of gears 41 drives the displacement of grinder 14 and second set of gears engaged with first set of gears 41 drives the displacement of grinding roller 31. This may ensure synchronized grinding. First set of gears angularly displace in a direction which is opposite to the second set of gears. Ground batter may be transferred by a collector tube into a collector communicably coupled to grinder 14. A vacuum or suction device, such as a pump or pneumatic pressure source may be coupled with resting unit 21 for sucking or otherwise driving the fermented batter out of resting unit 21.

Example embodiment grinding device 10 may include a programmable control with a display interface which allows user to operate the device. The display interface may show the weight of the different ingredients, selection menu, temperature inside the device and timer. This data may be derived from a load sensor or a weighing balance which transfers data to the interface.

A self-cleaning system may clean automatic grinding device 10 through pipes, nozzles, brushes, and/or soap dispenser 26d within automatic grinding device 10. The cleaning action may be based on pressure or steam-based cleaning, for example. Device 10 may be programmed for self-cleaning at least two times during one complete grinding process. A first cleaning process may be a pre-cleaning process before the ingredients are added to grinder 14, and only water may be used for rinsing grinder 14 and roller 31 in this pre-cleaning. Used water may be drained out after rinsing into drain 35. A second cleaning process, a post-grinding cleaning, may start after the ingredients are ground and the resultant batter is dispensed into resting unit 21, wherein soap dispenser 26d incorporated within device 10 dispenses soap into water. This wash cycle includes water and soap suspension directed into grinder 14 and roller 31, with fixed retention time and further replenished with continuous spraying of water to rinse any residual batter or soap. Water from water storage 26c may supply water spray channels 33 with water to spray into grinder 14. Soap from dispenser 26d may also be used. Grinder 14 may automatically rotate, agitate, and/or tilt while being cleaned. Optionally brushes may scrub grinder 14 from inside. Brushes may be provided in frame 50 for being lowered into grinder 14 while it is being cleaned. Soap from the soap dispenser 26d is fed into the grinding drum through openings in the frame above grinder 14.

The used water is drained into drain 35. Drain 35 is located operatively below grinder 14 in a manner such that when grinder 41 tilts to a certain degree, dirty water drains into the drain 35. Drain 35 may be located operatively below grinder 41 in a manner such that when grinder 14 tilts to a certain degree, the mixture to be drained can spill over into the drain 35. Drain 35 may be offset, in its axis, with respect to grinder 41. Drain 35 is connected to drain pipe 37 which drains out the water collected.

Wet grinding may require large amounts of water, and grinder 14 may receive correct amounts of water at correct intervals in example embodiment device 10. This may reduce or prevent ingredient dry up, motor overload, and heatup of grinding stones. After a start of a grinding process, water, at regular intervals, may be fed through the water spray channels 33 to keep the grinder wet, potentially based on a desired wetness of output batter.

Example embodiment automatic grinding device 10 may be wirelessly connected over a network to a remote device for analysis and feedback. The remote device may include, but not limited to, a computer, or a tablet or a smart phone. The user may download an application also called program/ software on the remote device. The network may be any suitable networks or links, including, but not limited to, a local area network LAN, wide area network WAN, Ethernet, an intranet or any wireless communication links. Similarly, device 10 may be controlled by a user by a user-interface. An example of operation may include adding ingredients into storage 26, setting batter parameters using the user interface, a pre-cleaning process, automatic addition of the ingredients in designated amounts to grinder 41 based on user input, grinding of the ingredients, dispensing of the ground ingredients into resting unit 21, a post-grinding cleaning process, and fermentation of the ground ingredients in resting unit 21.

FIGS. 11-17 illustrate an example embodiment grinder 14a with inner drum 102 and external drum 104 along with grinding roller 31. Typically, inner drum 102 angularly displaces or rotates while external drum 104 is fixed, similar to a washer mechanism. Motor 106 is fixed, on top, of the grinding system to angularly displace inner drum 102. Inner drum 102 includes opening 108 at its operative base to dispense ground batter as well as to dispense rinsed water after cleansing of the inner drum. Inner drum 102 is angularly displaceable or rotatable about an axis.

FIG. 13 is an alternative configuration with of grinding roller 14a including grinding stones 31, which may be freely angularly displaceable about their central axis. Grinding roller 14a may be rotatable about an axis of shaft 110. Shaft 110 may extend from the motor 106 holding grinding roller 14a and driven by motor 106. Scrapper 109 may scrape batter off the inner walls of inner drum 102 while shaft 110 is rotating. Scrapper 109 may be coupled to shaft 110 through another shaft in a manner such that it is offset and radially spaced apart from the central axis of inner drum 102. In this way, a lateral edge of scrapper 109 scrapes the inner wall of inner drum 102 to scrape off any and all batter. Grinding roller 14a may be rotated opposite of inner drum 102 on a same axis of rotation. Shaft 110 of roller 14a ends, at its operative bottom, in base plate 114 with female connectors so as to receive the clutch and lock of FIG. 16.

Inner drum 102 may be driven by a top motor, which ensures that opening 108 aligns with the dispensing pump of FIG. 14 to dispense ground batter or to dispense rinsed water to cleanse the drum. An iris gate may be used for opening and closing opening 108 with respect to the dispensing pump of FIG. 4. Additionally, a proximity sensor may be placed adjacent to opening 108 and dispensing pump inlet so that a proximity signal may be sent to the top motor driving the inner drum's angular displacement so as to ensure that the inner drum 102 stops exactly when its opening is aligned with the dispensing pump entry point. A stepper motor may disengage the male connector from the female connector, thereby separating corresponding shafts. This may achieve alignment of an iris gate in inner drum 102 with a dispensing pump. Once the openings are aligned, the top motor starts again and, at this time, only the grinding rollers rotate so that scrapper 109 scrapes out the batter toward opening 108 into the dispensing pump while the inner drum remains stationary. Motor 106 may be a pancake and a direct drive motor, for example.

FIG. 14 illustrates dispensing pump 120 configured to selectively dispense ground batter or water from inner drum 102 into respective storages or resting unit 21 for ground batter though corresponding outlets of the dispensing pump. Dispensing pump 108 may be located at an operative bottom of inner drum 102. During cleaning, draining, and dispensing, this pump may be switched on to allow contents of the drum to flow through.

Dispensing pump 108 may include an input 108a which receives ground batter or rinsed water from inner drum 102. Depending upon content, batter release valve 108b or water release valve 108c may be opened. Inlet 108a extends to a common pipe which, then, splits into batter release pipe 108d and water release opening 108e. A batter storage mechanism or resting unit 21 receives ground batter from inner drum 102 through the dispensing pump 108.

As shown in FIG. 16, clutch and locking system 130 is provided at the operative bottom of inner drum 102. Clutch and locking system 130 includes a base motor stepper motor 132 with an engaging stub 134 protruding outside of base motor 132. Engaging stub 134 is a threaded stub configured to move in and out of base stepper motor 132 enclosure so as to effect engaging and disengaging of inner drum 102 with motor 132. Stepper motor 132 helps to align the male connectors with the female connectors. Bearing holder 136 may engage co-axially with the stepper motor 132 and the engaging stub 134 in order to hold a bearing 138 which enables angular displacement of the inner drum 102. Inner drum 102 is co-axially and concentrically fitted with this inner ring of bearing 138 so that as the bearing linearly displaces due to the top motor action, the inner drum 102 simultaneously and concurrently linearly displaces. An operative top plate 142 with operatively upwardly male connectors 144 may be co-axial with the bearing 138 and engage with the bearing 138 through a shaft extending operatively downward from top plate 142 and fits within the inner diameter of the bearing 138. As the inner ring angularly displaces, the inner drum angularly displaces.

During operation for making ground batter, the clutch and locking system 130 effects an engagement of the male connectors 144, of the clutch and locking system 130, with the female connectors 114, of the shaft of grinding roller 14a, by pushing the engagement stub 134 operatively upward. During operation before dispensing ground batter, to angularly displace the inner drum 102, to a synchronized position, the engagement stub 134 retracts, thereby spacing apart, or disengaging, the male connectors 144, of the clutch and locking system 130, with the female connectors 114, of the shaft of modified grinding roller 14a. Thus, in the disengaged position, when grinding stops, modified roller 14a may angularly displace freely, while the inner drum 102 is driven by the motor towards the position where it aligns with the dispensing pump 120.

When the grinding process starts, the clutch and transmission engages with a bush of the inner drum and grinding roller. During this step, the inner drum will angularly displace itself. Once the batter formation is completed, the clutch mechanism disengages and only the grinding roller and a scrapper connected to the shaft will angularly displace. A door, is provided, in the inner rotating drum which opens and which connects to the dispensing pump. A valve opens automatically with the help of solenoid to allow batter to be dispensed on to the resting unit. During this operation, the modified grinding roller 14a will be angularly displacing. With the help of the scrapper 109 that is attached to the grinding roller, all the batter is pushed out of the opening/door of the inner drum 102 which is placed at the operative bottom. Once all the batter is pushed out, the door closes, dispensing valve closes, and the pump shuts off. Then, pressurized water is sprayed on to the inner drum for cleaning. Motor stops for a moment with an integrated braking mechanism in the motor. The clutch engages to lock the bush male and female connectors with the inner grinding drum to angularly displace. Then, the door in the drum opens to let the dirty water to be drained. The pump opens and a drain is opened to let the dirty water drained through the drain pipe connected to the drain valve and to the draining of the device. Once this process is completed, the motor stops and the valves go back to the lock position.

It will be appreciated by one skilled in the art that example embodiments may be varied through routine experimentation and without further inventive activity. For example, although a wet grinder is described, it is understood that other fluids, or a relatively dry grind, are useable with the wet grinder. Variations are not to be regarded as departure from the spirit and scope of the exemplary embodiments, and all such modifications as would be obvious to one skilled in the art are intended to be included within the scope of the following claims.

What is claimed is:

1. An automated grinder system, comprising:
   a storage configured to store an ingredient, wherein the storage includes a selective closure to retain water for soaking the ingredient without leakage and to release the ingredient after a soaking period;
   a grinder connected to the storage so as to receive the ingredient from the storage, wherein the grinder includes a rotatable inner drum, a fixed external drum, and a grinding roller configured to form the soaked ingredient into a ground batter; and
   a resting unit configured to receive the ground batter from the grinder, wherein the resting unit is configured to heat the ground batter for fermentation.

2. The grinder system of claim 1, further comprising:
   a water storage configured to hold water, wherein the water storage is connected to the storage so as to selectively release water for soaking the ingredient into the storage; and
   a plurality of water spray channels feeding from the water storage, wherein the water spray channels are directed into the grinder so as to spray water into the grinder.

3. The grinder system of claim 1, wherein the grinder is configured to rotate about a first axis when grinding, and wherein the grinder is configured to rotate about a second axis different from the first axis when draining the ground batter.

4. The grinder system of claim 3, further comprising:
   a first motor configured to drive the grinder about the first axis; and
   a second motor configured to drive the grinder about the second axis.

5. The grinder system of claim 3, wherein the grinder selectively connects to the resting unit to drain by rotating about the second axis.

6. The grinder system of claim 1, wherein the storage includes a motor driving a flap that seals an opening of the storage, and wherein movement of the flap by the motor causes the ingredient to move into the grinder.

7. The grinder system of claim 1, further comprising:
   a suction pump configured to drive the batter out of the resting unit.

8. The grinder system of claim 1, further comprising:
   a soap dispenser configured to dispense soap into the grinder.

9. The grinder system of claim 1, wherein the storage includes a drain to separately drain out waste water from the ingredient after a soaking cycle is complete.

10. The grinder system of claim 9, wherein the drain includes a sieve valve at a bottom of the storage and a seal valve connected to separate pipes from the sieve valve.

11. The grinder system of claim 1, wherein the grinder includes a rotatable shell and the grinder roller includes a plurality of grinding stones attached to an end of a rotatable shaft extending into the rotatable shell, and wherein the rotatable shell and the rotatable shaft are configured to rotate in opposite directions about a same axis of rotation.

12. The grinder system of claim 1, wherein the resting unit is further configured to cool, humidify, or dehumidify the ground batter.

13. The grinder system of claim 1 further comprising:
a drain; and
a dispensing pump at a bottom of the inner drum configured to dispense, from the inner drum, ground batter to the resting unit or rinsed water to the drain in a selective and controlled manner.

14. The grinder system of claim 1, further comprising:
a clutch and locking system configured to engage a shaft of the grinder assembly so that the inner drum and the shaft rotate together and to disengage the shaft of the grinder assembly so that the shaft rotates alone rotates without the inner drum.

15. The grinder system of claim 1, wherein the inner drum includes an opening at its base to dispense ground batter and rinsed water.

16. The grinder system of claim 1, wherein the grinder assembly includes a scrapper configured to scrape batter off inner walls of the inner drum.

17. The grinder system of claim 1, wherein the grinder assembly includes a roller extending into the internal drum, and wherein the roller is configured to rotate opposite of the inner drum.

18. The grinder system of claim 1, wherein the storage includes a motor driving a flap that seals an opening of the storage, and wherein movement of the flap by the motor causes the ingredient to move into the grinder.

19. The grinder system of claim 1, further comprising:
a soap dispenser configured to dispense soap into the grinder.

20. The grinder system of claim 1, wherein the storage includes a drain to separately drain out waste water from the ingredient after a soaking cycle is complete.

21. The grinder system of claim 20, wherein the drain includes a sieve valve at a bottom of the storage and a seal valve connected to separate pipes from the sieve valve.

22. The grinder system of claim 1, wherein the resting unit is further configured to cool, humidify, or dehumidify the ground batter.

23. The grinder system of claim 1 wherein, the dispensing pump includes a batter release valve, a water release valve, and an inlet configured to receives ground batter or rinsed water from the inner drum, wherein the inlet extends to a common pipe that splits into a batter release pipe and a water release opening.

24. The grinder system of claim 1, further comprising:
a water reservoir connected to the storage, wherein,
the grinder is connected to the storage and the water reservoir so as to receive water and the ingredient, wherein the grinder a first component coaxial with and rotatable independently from a second component, and wherein the ingredient is held between the first component and the second component for grinding the ingredient into a ground batter, and
the resting unit is configured to receive the ground batter from the grinder, wherein the resting unit is configured to humidify and heat the ground batter for fermentation.

25. The grinder system of claim 24, further comprising:
a plurality of water sprays directed into the grinder and connected to the water reservoir for cleaning the grinder.

* * * * *